United States Patent
Austin et al.

(10) Patent No.: US 8,899,234 B2
(45) Date of Patent: Dec. 2, 2014

(54) CPAP MASK FRAME

(75) Inventors: Gary Austin, Euclid, OH (US); James Timothy Austin, Concord Township, OH (US)

(73) Assignee: Home Health Medical Equipment, Inc., Saint Louis, MO (US)

(*) Notice: Subject to any disclaimer, the term of this patent is extended or adjusted under 35 U.S.C. 154(b) by 696 days.

(21) Appl. No.: 13/117,273

(22) Filed: May 27, 2011

(65) Prior Publication Data

US 2011/0297158 A1    Dec. 8, 2011

Related U.S. Application Data

(60) Provisional application No. 61/350,958, filed on Jun. 3, 2010.

(51) Int. Cl.
*A61M 11/00* (2006.01)
*A61M 16/06* (2006.01)

(52) U.S. Cl.
CPC .......... *A61M 16/0633* (2013.01); *A61M 16/06* (2013.01); *A61M 16/0611* (2013.01); *A61M 16/0683* (2013.01)
USPC ............. 128/206.21; 128/205.25; 128/207.11

(58) Field of Classification Search
USPC ............. 128/205.25, 206.11–206.28, 207.11, 128/207.13
See application file for complete search history.

(56) References Cited

U.S. PATENT DOCUMENTS

| | | | | |
|---|---|---|---|---|
| 5,542,128 | A * | 8/1996 | Lomas | ................................ 2/173 |
| 6,860,269 | B2 | 3/2005 | Kwok et al. | |
| 7,000,614 | B2 * | 2/2006 | Lang et al. | ............... 128/206.21 |
| 7,100,610 | B2 * | 9/2006 | Biener et al. | ............. 128/206.21 |
| 7,654,263 | B2 | 2/2010 | Lang et al. | |
| 7,665,464 | B2 * | 2/2010 | Kopacko et al. | ......... 128/206.24 |
| 8,210,180 | B2 * | 7/2012 | Gunaratnam | ............ 128/206.24 |
| 8,353,294 | B2 * | 1/2013 | Frater et al. | ............. 128/207.11 |
| 2003/0019496 | A1 * | 1/2003 | Kopacko et al. | ......... 128/206.24 |
| 2010/0059058 | A1 * | 3/2010 | Kuo | .......................... 128/205.25 |
| 2010/0071700 | A2 * | 3/2010 | Hitchcock et al. | ........ 128/207.11 |
| 2013/0000646 | A1 * | 1/2013 | Haibach | .................... 128/205.25 |

OTHER PUBLICATIONS

International Search Report and Written Opinion issued Feb. 27, 2012 in corresponding PCT Application No. PCT/US2011/038689.

* cited by examiner

*Primary Examiner* — Steven Douglas
(74) *Attorney, Agent, or Firm* — Pearne & Gordon LLP

(57) ABSTRACT

A continuous positive airway pressure ("CPAP") mask is provided. The CPAP mask includes a mask support that includes a cavity provided within the mask support. The CPAP mask further includes a mask cushion that is received within the cavity. The mask cushion and the mask support each include an opening. Air can pass from an air delivery tube through the openings and into the mask cushion. The mask cushion can be placed around a patient's breathing orifice to deliver the air to the patient. The CPAP mask further includes a forehead support that is spaced apart form the mask support. A neck portion attaches the forehead support to the mask support. The neck portion is flexible and is molded to both the mask support and the forehead support. The flexible neck portion allows the mask support to move with respect to the forehead support.

8 Claims, 4 Drawing Sheets

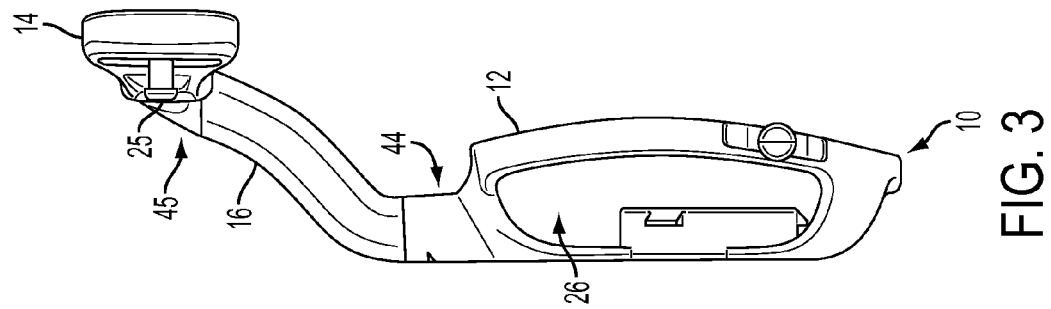
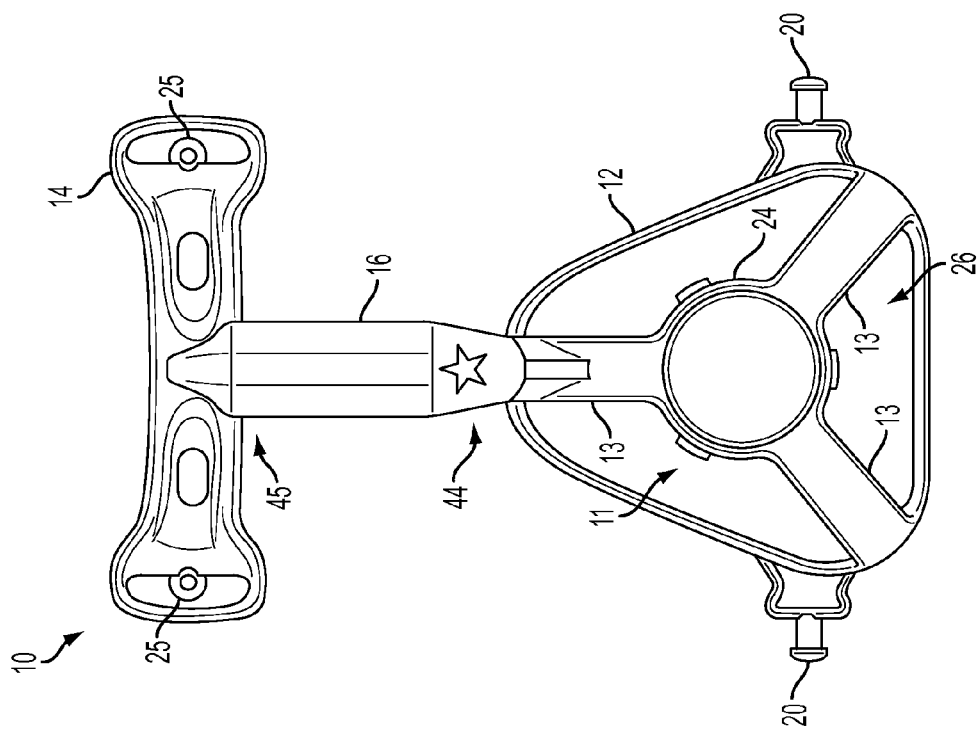

CPAP MASK FRAME

CROSS-REFERENCE TO RELATED APPLICATIONS

This application claims priority to U.S. provisional patent application No. 61/350,958, filed on Jun. 3, 2010, the disclosure of which is expressly incorporated herein by reference for all purposes.

FIELD

The present invention relates generally to ventilation devices, and more particularly, to a continuous positive airway pressure ("CPAP") nose mask.

BACKGROUND

CPAP masks are commonly used to treat patients suffering from sleep apnea. A CPAP mask may be placed over a patient's face while sleeping to deliver air to the patient through the mask. The CPAP mask may cover a patient's nose and/or mouth during sleep to form a seal and ensure proper air flow. Straps can be used to hold the CPAP mask in place. Thus, a user can wear the CPAP mask and sleep with a steady supply of air flow throughout the night while the mask remains secure. The size of each patient's face can vary, however, preventing the CPAP mask from properly fitting a wide range of patients. This can cause a number of problems, such as air leakage from the mask, pain and discomfort during use, decreased effectiveness, etc. Varying mask sizes (small-large, etc.) may be used, but problems still persist, such as when the straps are tightened unevenly. Therefore, there is a continuing need for a comfortable and easily adjustable CPAP mask.

BRIEF SUMMARY

The following presents a simplified summary in order to provide a basic understanding of some example aspects. This summary is not an extensive overview. Moreover, this summary is not intended to identify critical elements nor delineate the scope. The sole purpose of the summary is to present some concepts in simplified form as a prelude to the more detailed description that is presented later.

In accordance with one aspect, a continuous positive airway pressure ("CPAP") mask is provided comprising a rigid mask support, a mask cushion coupled to the mask support, the mask cushion and the mask support each including an opening, wherein air is configured to pass through the opening and into the mask cushion, a rigid forehead support spaced apart from the mask support, and a flexible neck portion integrally molded between the forehead support and the mask frame.

In accordance with another aspect, a continuous positive airway pressure ("CPAP") mask is provided comprising a mask support made from a first material, a forehead support made from the first material and spaced apart from the mask support, a forehead support attachment structure extending from the forehead support, the forehead support attachment structure including at least one attachment structure, and a neck portion made from a second material, wherein the first material and the second material are joined at the forehead support attachment structure by a mechanical bond.

In accordance with another aspect, a method is provided for fabricating a continuous positive airway pressure ("CPAP") mask, comprising the steps of molding a mask support out of a first material, molding a forehead support out of the first material, and molding a neck portion out of a second material, wherein the neck portion is overmolded onto corresponding portions of the mask support and the forehead support.

BRIEF DESCRIPTION OF THE DRAWINGS

The foregoing and other aspects will become apparent to those skilled in the art upon reading the following description with reference to the accompanying drawings, in which:

FIG. 2 illustrates a front elevation view of an example CPAP mask frame;

FIG. 3 illustrates a side elevation view of the example CPAP mask frame;

DETAILED DESCRIPTION

Figure 1:
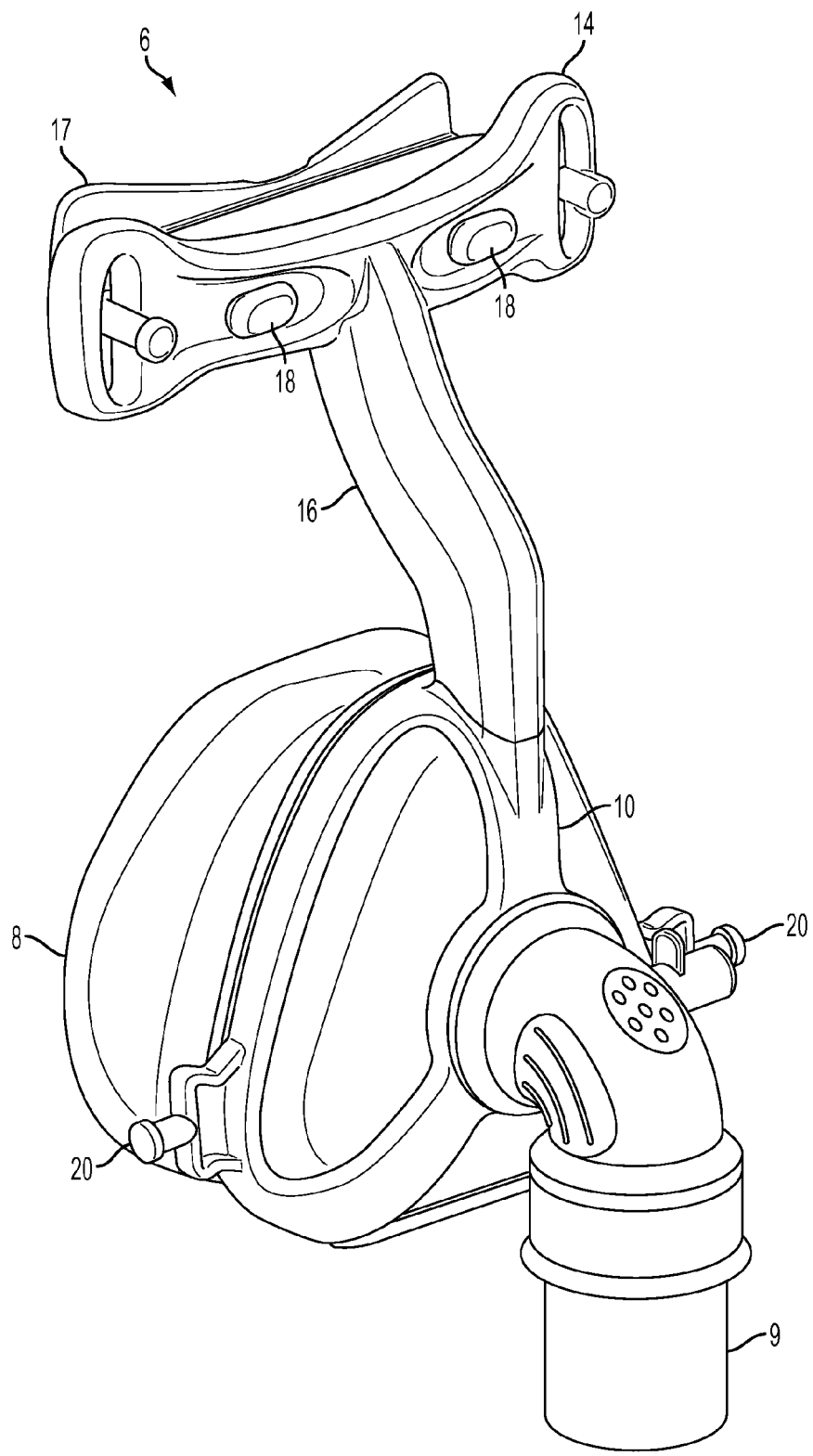
FIG. 1 illustrates a perspective view of an example continuous positive airway pressure ("CPAP") mask.

Example embodiments that incorporate one or more aspects are described and illustrated in the drawings. These illustrated examples are not intended to be a limitation on the present embodiments. For example, one or more aspects of the present embodiments can be utilized in other embodiments and even other types of devices. Moreover, certain terminology is used herein for convenience only and is not to be taken as a limitation on the present embodiments. Still further, in the drawings, the same reference numerals are employed for designating the same elements.

Turning to the shown example of FIG. 1, an example continuous positive airway pressure ("CPAP") mask 6 is shown. The CPAP mask 6 can be used to facilitate delivery of air, such as oxygen, an oxygen mixture, gas or the like, to a patient's nose and/or mouth. The CPAP mask 6 can include a mask cushion 8 attached to a mask frame 10. The mask cushion 8 can be designed to fit over the nose of a patient. An air delivery tube 9 can be attached to the mask cushion 8 and the mask frame 10. Air can be delivered through the air delivery tube 9. As such, air can be delivered to the patient during sleep from the air delivery tube 9 and through the mask cushion 8 to the patient's nose. Attachment structures (not shown), such as straps, bands, or the like, can be used to removably and/or flexibly attach the CPAP mask 6 to the patient's face, as will be described in more detail below.

It is to be understood that varying examples of the CPAP mask 6 can incorporate some, or all, of the features described herein. For instance, the CPAP mask 6 may be a full face mask (not shown) as opposed to merely fitting over the nose of a patient. In such an example, the CPAP mask 6 may be large enough to cover both the nose and the mouth of the patient. As such, the figures and description of the CPAP mask 6 described herein are not intended to limit the structure of the CPAP mask 6, and a number of different examples and variations of the CPAP mask 6 are contemplated.

Referring now to FIGS. 2 and 3, the mask frame 10 of the CPAP mask 6 is shown. The mask frame 10 can include a mask support 12. The mask support 12 can define an outer boundary of the mask frame 10. As shown, the mask support 12 includes a boundary portion that is generally triangular in shape, however other shapes are contemplated. For instance, the mask support 12 could include a number of different shapes, including, but not limited to circular shapes, oval shapes, rectangular shapes, or the like. Similarly, the mask support 12 can include a variety of different sizes, and is not limited to the size and proportion shown in the examples. For instance, the mask support 12 can be small enough to receive and/or fit around a patient's nose. Similarly, in another example, the mask support 12 could be large enough to receive and/or fit around both the nose and mouth of the patient, or just the mouth of the patient. The mask support 12 can be formed from a first material. The first material can include a variety of different materials, such that the mask support 12 can be a rigid structure. The first material can include, but is not limited to, a plastic material, or the like.

The mask support 12 can include one or more projecting portions 13 that can provide stability and/or support to the mask support 12. In the shown example, the projecting portions 13 include three projecting portions, however more or fewer projecting portions are contemplated. The projecting portions 13 can extend between an outer perimeter of the mask support 12 towards a center portion 11 of the mask support 12. The projecting portions 13 include a rigid material that can form a back surface of the mask support 12. The mask support 12 is not limited to the projecting portions 13 as shown, and, in a further example, can include a solid, fully formed back surface instead of the projecting portions 13.

The center portion 11 of the mask support 12 can further include an opening 24. The opening 24 can be formed at an intersection of the projecting portions 13 at a back surface of the mask support 12. The opening 24 is shown to be substantially circular, however a number of sizes and shapes are contemplated, such as square, rectangular, oval, or the like. The opening 24 can be attached to the air delivery tube 9 (shown in FIG. 1) at one side. The opening 24 can be sized to have a diameter that corresponds with a diameter of the air delivery tube 9. The opening 24 can form a seal, such as an air-tight seal, with the air delivery tube 9. As such, air can pass from the air delivery tube 9 and through the opening 24 without escaping from the attachment between the opening 24 and the air delivery tube 9.

The mask support 12 and the projecting portions 13 can, together, define a cavity 26 formed within the mask support 12. The cavity 26 may be sized to fit around a patient's nose and/or mouth, though multiple sizes (i.e., small, medium large, etc.) may be provided to accommodate varying face sizes. The cavity 26 can be sized to receive the mask cushion 8. The opening 24 can define a path for the passage of air from an exterior location, through the opening 24, and into the cavity 26.

Referring back to FIG. 1, the mask cushion 8 can be inserted and attached to the mask support 12. Specifically, the mask cushion 8 can be attached within the cavity 26. The mask cushion 8 includes an opening (not shown) that is sized to substantially match the size of the opening 24. A periphery of the mask cushion 8 is configured to create a seal between the patient's face and the mask. The mask cushion 8 may be made of a number of materials, such as an elastomer, rubber, or the like, and may substantially fill the cavity 26. The mask cushion 8 can further provide a delivery area for the air. The air delivery tube 9, opening 24, and opening in the mask cushion 8 can each be sized to have corresponding diameters.

Both the air delivery tube 9 and mask cushion 8 can be attached, such as sealingly attached, to the opening 24. Similarly, the air delivery tube 9 and the mask cushion 8 can be attached, such as sealingly attached, to each other. As such, air can be delivered through the air delivery tube 9, through the opening 24, and into the mask cushion 8. Air within the mask cushion 8 can pass to the patient with minimal leakage.

The mask frame 10 can further include one or more connectors 20. The connectors 20 can be attached at a variety of locations within the mask frame 10, but are shown to extend from the mask support 12. The connectors 20 are not limited to the location of the shown example, and can extend from a variety of locations along the mask support 12. The shown examples include two connectors, however, it is to be understood, that more connectors or fewer connectors can be provided. Similarly, the connectors are shown to be project outwardly as a screw shape, but can take on a number of different structures as well. Straps, bands, or the like, can be attached to the connectors 20. The straps can wrap around a patient's head to secure the mask frame 10 to a patient's face.

Figure 6:
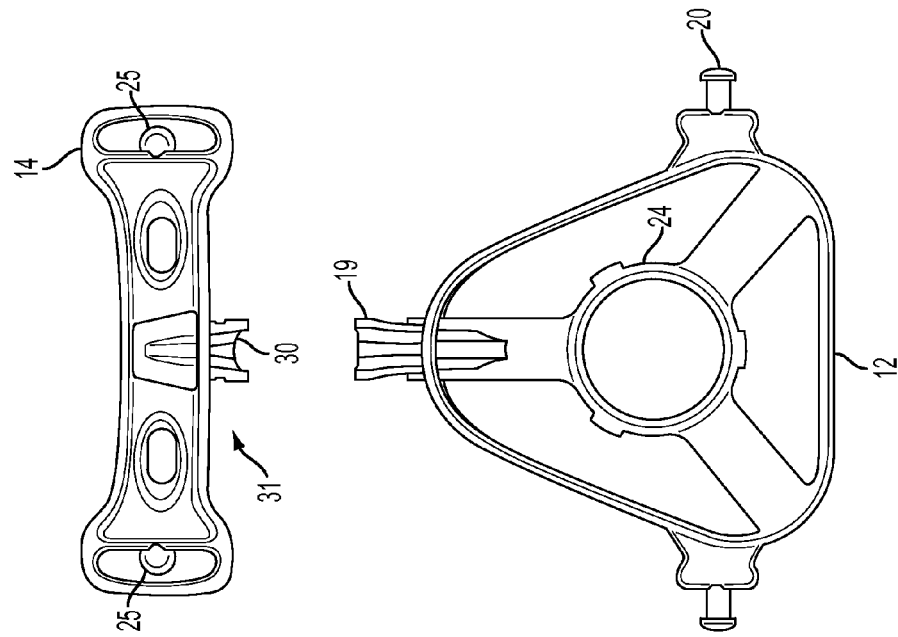
FIG. 6 illustrates a rear elevation view of the example CPAP mask frame including the mask support and the forehead support.
Figure 5:
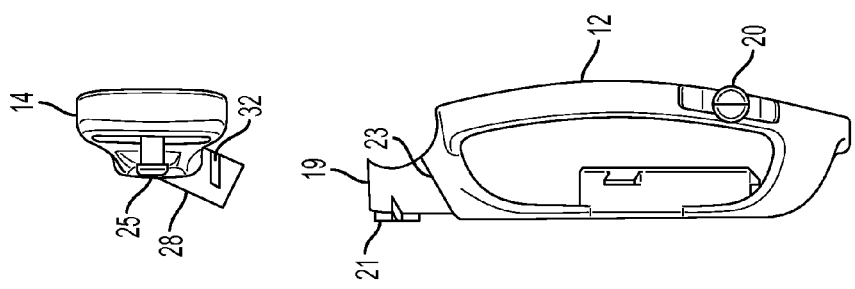
FIG. 5 illustrates a side elevation view of the example CPAP mask frame including the mask support and the forehead support.
Figure 4:
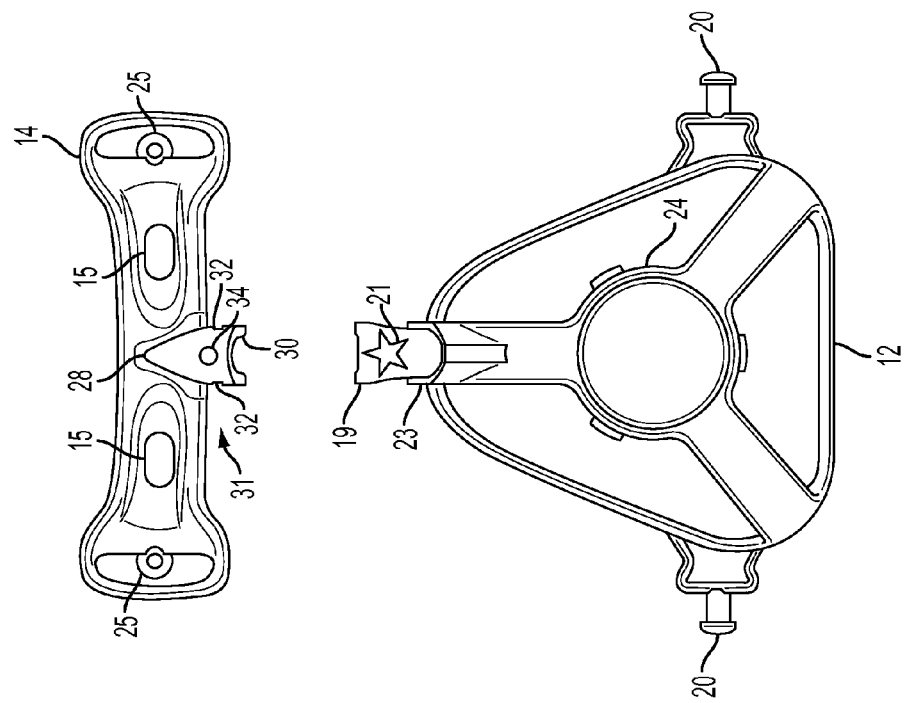
FIG. 4 illustrates a front elevation view of the example CPAP mask frame including a mask support and a forehead support.

Turning now to FIGS. 4 to 6, the mask frame 10 may further include a mask support attachment structure 19. The mask support attachment structure 19 can assist in attaching the mask support 12 to a neck portion 16. The mask support attachment structure 19 may project outwardly from the mask support 12 and can include a protrusion 21 formed on the mask support attachment structure 19. In the shown examples of FIGS. 3 and 4, the protrusion 21 is star-shaped, but a number of different shapes and sizes are possible, such as a square shape, a triangle shape, etc. As will be discussed below, the protrusion 21 can assist in attaching the neck portion 16 to the mask support attachment structure 19. The mask support attachment structure 19 can be formed from the same material as the mask support 12. In one example, the mask support 12 and mask support attachment structure 19 can include a plastic molded frame, such as a poly-carbonate, though a number of different materials are contemplated. In the alternative, the mask support attachment structure 19 could be formed from a different structure.

The mask support attachment structure 19 can further include a mounting surface 23. The mounting surface 23 can be formed at an intersection of the mask support attachment structure 19 and the mask support 12. As shown in FIG. 4, the mounting surface 23 can be slightly larger in diameter than the mask support attachment structure 19, and can extend from a top surface to a bottom surface of the mask support attachment structure 19. The mounting surface 23 is shown to project at an angle with respect to the mask support 12 and mask support attachment structure 19. The mounting surface 23 is not limited to the angle of the shown example, and can extend at a larger or smaller angle.

The mask frame 10 can further include a forehead support 14. The forehead support 14 can align with a patient's forehead while the mask support 12 and mask cushion 8 fit around a patient's nose. The forehead support 14 may include a variety of geometries, such as a flat, elongated shape and/or may be curved so as to match the contours of a patient's forehead. The forehead support 14 can be formed from the first material. The first material can be similar and/or identical to the first material of the mask support 12. As with the mask support 12, the first material can include a variety of different materials, such that the forehead support 14 can be a rigid structure. The first material can include, but is not limited to, a plastic material, or the like. In an alternative example, the forehead support 14 can be formed from a third material that is different from the first material of the mask support 12.

The forehead support 14 may include a cushion 17 (FIG. 1), such as a pad, or the like 17 to improve comfort and adaptability of the forehead support 14. The cushion 17 can be made from a flexible material such as a silicone elastomer or the like. The cushion 17 can be attached to the forehead support 14, such that the cushion 17 is positioned between the forehead support 14 and the patient's forehead. The cushion 17 may include protrusions 18 allowing for the cushion 17 to be held in place, such as by a snap-fit engagement, with holes 15 in the forehead support 14.

The forehead support 14 can include one or more connectors 25. The connectors 25 are shown to be positioned on opposing sides of the forehead support 14. The connectors 25 can be similar or identical to the connectors 20 positioned on the mask support 12. The connectors 25 can project outwardly from the forehead support 14 and can have a cylindrical boss shape, but a number of other shapes and structures, such as elongated apertures, are contemplated as well. The connectors 25 can project perpendicularly from the forehead support 14. For instance, the forehead support 14 can extend along a first plane while the connectors 25 extend along a second plane that is substantially perpendicular to the first plane of the forehead support 14. The straps can be attached to the connectors 25. As such, the straps can be attached to both sets of connectors 20, 25, such that the straps can wrap around the patient's head to secure the mask frame 10 to a patient's nose.

The forehead support 14 can further include a forehead support attachment structure 28 for attaching to the neck portion 16. The forehead support attachment structure 28 can be positioned substantially at a center point of the forehead support 14, however, the forehead support attachment structure 28 could be offset. The forehead support attachment structure 28 can be monolithically formed with the forehead support 14, or could be separately formed and attached to the forehead support 14. The forehead support attachment structure 28 can be formed from a plastic molded frame, such as a poly-carbonate, though a number of different materials are contemplated.

The forehead support attachment structure 28 may include one or more attachment structures 31, including slots, holes, openings, bores, or the like. Specifically, the attachment structures 31 can include one or more slots 32 positioned on the sides of the forehead support attachment structure 28. The attachment structures 31 can further include one or more holes 34 extending partially or completely through the forehead support attachment structure 28. The attachment structures 31 can further include a female bore 30 formed within the forehead support attachment structure 28. As will be described below, the slots 32, holes 34, and female bore 30 can assist in attaching the forehead support attachment structure 28 to a neck portion 16.

The CPAP mask 6 is not limited to the attachment structures shown and described herein. In further examples, the forehead support attachment structure 28 could include more, fewer, or alternate attachment structures that function similarly to the attachment structures 31 in the shown example. For instance, the one or more slots 32 could be positioned along a top and bottom surface of the forehead support attachment structure 28. In another example, holes 34 may include multiple holes, with holes positioned on side surfaces of the forehead support attachment structure 28. Similarly, the forehead support attachment structure 28 may not include a female bore 30 and, instead, may be a substantially solid structure with a filled center portion.

Figure 7:
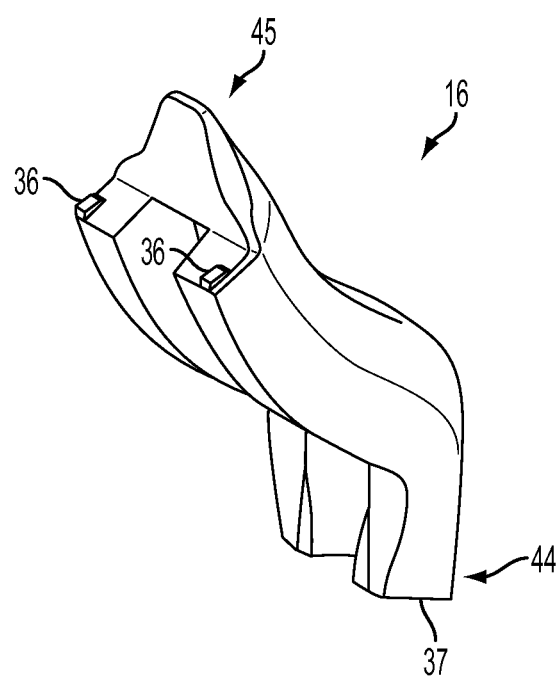
FIG. 7 illustrates a perspective view of an example neck portion of the CPAP mask frame.

Referring now to FIG. 7, the neck portion 16 is illustrated. The neck portion 16 can include an elongated structure that curves at a substantially 45° angle. It is to be understood that the neck portion 16 is not limited to the angle in the shown example, and could extend at one or more other angles. The neck portion 16 can include opposing ends, including a first end 44 and a second end 45. As will be described in more detail below, the first end 44 can be attached to the mask support 12 while the second end 45 can be attached to the forehead support 14.

The neck portion 16 may be formed from a second material. The second material can include a flexible material, such as an elastomeric material. It is to be understood that the neck portion 16 may be formed from a number of materials, such as a thermoplastic elastomer (TPE) with a 40 durometer Shore A. In further examples, a variety of materials and durometer measures are available depending on the application, including a range of rubbers, etc. The neck portion 16 can be flexible due to the material, such that the neck portion 16 can be flexed, twisted, or the like.

The second material can be overmolded onto the mask support 12 and forehead support 14. As such, the neck portion 16 can be integrally connected to the mask support 12 and forehead support 14. In this example, a single mold (not shown) may be used in the fabrication of the mask frame 10. The mold may be sized and shaped to match the desired dimensions of the mask frame 10. In the first step, a rigid material, such as a polycarbonate, may be injected into the mold to form the mask support 12 and forehead support 14. Next, after the mask support 12 and forehead support 14 have substantially solidified, the flexible material, e.g., elastomer, may be injected into the mold to form the neck portion 16. The elastomer can be injected into the mold at a position between the mask support 12 and forehead support 14. As such, the elastomer material fills in any gaps and/or surrounds the mask support attachment structure 19 and forehead support attachment structure 28. The elastomer engages the attachment structures 31 by flowing into the attachment structures 31, including the female bore 30, slots 32, and/or holes 34 of the forehead support attachment structure 28. The elastomer also engages the protrusion 21 and mask support attachment structure 19 by flowing around and covering the protrusion 21 and mask support attachment structure 19. The elastomer can also abut and/or contact the mounting surface 23. Accordingly, when the elastomer solidifies, the neck portion 16 is mechanically bonded directly to both the mask support 12 and forehead support 14. Thus, the mask frame 10 is formed of one integrally connected piece, including the mask support 12 connected to the forehead support 14 by the elastomeric neck portion 16.

In addition to the mechanical bond formed between the neck portion 16, mask support 12 and forehead support 14, a chemical bond may also be formed. During the overmolding process, a bond can be formed due to melting and/or chemical adhesion of the surfaces of the neck portion 16 to both the mask support attachment structure 19 and forehead support attachment structure 28. In such an example, melting and/or a chemical reaction may occur between the surfaces to form the bond. The strength of the bond may vary due to a number of factors, including the types of material used, melting points of the materials, etc. Upon solidifying, the chemical bond is formed, thus ensuring that the mask frame 10 is integrally connected as one piece.

In an alternate method of manufacture, the neck portion 16 can be formed separately from the mask support 12 and forehead support 14. Accordingly, the neck portion 16 can be formed such that the first end 44 can be attached to the mask support 12 and the second end 45 can be attached to the forehead support 14. For instance, the neck portion 16 may include one or more projections 36 at the second end 45 for insertion into the slots 32 of the forehead support attachment structure 28. Though not shown in the drawings, the neck portion 16 may further include a circular projection for insertion into the one or more holes 34. At an opposite end, the first end 44 of the neck portion 16 may include a star-shaped female receiving portion (not shown) for engaging with the protrusion 21. The first end 44 may also include an angled surface 37 for engaging with the mounting surface 23. The angled surface 37 can be sized and shaped to substantially match the angle of the mounting surface 23, such that the angled surface 37 and the mounting surface 23 are in close engagement with each other.

Once formed, the neck portion 16 is substantially s-shaped and can allow for the forehead support 14 to have some movement independent of the mask support 12. For instance, if the attachment structures (not shown) attached to the connectors 20, 25 are unevenly tightened, the neck portion 16 can provide for side to side torsion, thereby ensuring that the mask support 12 fits snugly over the patient's nose. Similarly, the mask support 12 and forehead support 14 can be moved along multiple axes while still maintaining the necessary control to provide resistance to the mask frame 10 and ensure seal integrity and proper internal pressure.

The invention has been described with reference to the example embodiments described above. Modifications and alterations will occur to others upon a reading and understanding of this specification. Examples embodiments incorporating one or more aspects of the invention are intended to include all such modifications and alterations.

What is claimed is:

1. A method for fabricating a continuous positive airway pressure ("CPAP") mask, comprising the steps of:
    molding a mask support out of a first material;
    molding a forehead support out of the first material, the mask support and the forehead support being separate and spaced apart; and
    molding a neck portion out of a second material, wherein the neck portion is overmolded onto corresponding portions of the mask support and the forehead support to connect the mask support to the forehead support.

2. The method of claim 1, further including the method step of providing the forehead support with at least one attachment structure.

3. The method of claim 2, wherein the second material includes an elastomeric material, further wherein the elastomeric material flows around the at least one attachment structure.

4. The method of claim 1, further including the method step of forming a chemical bond between the neck portion and the mask support and forming a chemical bond between the neck portion and the forehead support.

5. A method for fabricating a continuous positive airway pressure ("CPAP") mask, comprising the steps of:
    molding a mask support out of a first material;
    molding a forehead support out of the first material; and
    molding a neck portion out of a second material, wherein the neck portion is overmolded onto corresponding portions of the mask support and the forehead support,
    wherein the neck portion molded out of the second material is a sole connection between the mask support and the forehead support.

6. The method of claim 5, further including the method step of providing the forehead support with at least one attachment structure.

7. The method of claim 6, wherein the second material includes an elastomeric material, further wherein the elastomeric material flows around the at least one attachment structure.

8. The method of claim 5, further including the method step of forming a chemical bond between the neck portion and the mask support and forming a chemical bond between the neck portion and the forehead support.

\* \* \* \* \*